US010093958B2

(12) United States Patent
Fourmestraux et al.

(10) Patent No.: US 10,093,958 B2
(45) Date of Patent: Oct. 9, 2018

(54) METHOD FOR THE DIFFERENTIAL ENUMERATION OF LACTIC ACID BACTERIA IN A MIXTURE IN A FOOD PRODUCT

(71) Applicant: Compagnie Gervais Danone, Paris (FR)

(72) Inventors: Candice Fourmestraux, Le Plessis Robinson (FR); Jerôme Combrisson, Grenoble (FR); Mickaël Boyer, Saint Cyr L'école (FR); Anna Galat, Villejuif (FR); Leyla Boumghar-Bourtchai, Shanghai (CN)

(73) Assignee: Compagnie Gervais Danone, Paris (FR)

( * ) Notice: Subject to any disclaimer, the term of this patent is extended or adjusted under 35 U.S.C. 154(b) by 0 days.

(21) Appl. No.: 15/103,253

(22) PCT Filed: Dec. 16, 2014

(86) PCT No.: PCT/FR2014/053359
§ 371 (c)(1),
(2) Date: Jun. 9, 2016

(87) PCT Pub. No.: WO2015/092258
PCT Pub. Date: Jun. 25, 2015

(65) Prior Publication Data
US 2016/0298163 A1    Oct. 13, 2016

(30) Foreign Application Priority Data
Dec. 16, 2013   (WO) ................ PCT/FR2013/060988

(51) Int. Cl.
*C12Q 1/14*   (2006.01)
*C12Q 1/04*   (2006.01)
*C12Q 1/08*   (2006.01)
*G01N 33/02*  (2006.01)

(52) U.S. Cl.
CPC ............ *C12Q 1/14* (2013.01); *C12Q 1/04* (2013.01); *C12Q 1/045* (2013.01); *C12Q 1/08* (2013.01); *G01N 33/02* (2013.01); *G01N 2333/315* (2013.01); *G01N 2333/335* (2013.01)

(58) Field of Classification Search
CPC .................................................... C12Q 1/045
See application file for complete search history.

(56) References Cited

FOREIGN PATENT DOCUMENTS

WO    2008/003810 A1    1/2008

OTHER PUBLICATIONS

Restaino et al. J of Food Protection, 2006, 69(2):315-322.*
Chevalier et al., "X-alpha-Gal-based medium for simultaneous enumeration of bifidobacteria and lactic acid bacteria in milk," Journal of Microbiological Methods, 13: 75-83 (1991).
Kneifel et al., "An X-Glu Based Agar Medium for the Selective Enumeration of Lactobacillus acidophilus in Yogurt-related Milk Products," International Dairy Journal, 3: 277-291 (1993).
Ashraf et al., "Selective and differential enumerations of *Lactobacillus delbrueckii* subsp. bulgaricus, *Streptococcus thermophilus*, *Lactobacillus acidophilus*, *Lactobacillus casei* and *Bifidobacterium* spp. in yoghurt—A review," International Journal of Food Microbiology, 149: 194-208 (2011).
Manafi, "New developments in chromogenic and fluorogenic culture media," International Journal of Food Microbiology, 60: 205-218 (2000).
Tharmaraj et al., "Selective Enumeration of *Lactobacillus delbrueckii* ssp. bulgaricus, *Streptococcus thermophilus*, Lactobacillus acidophilus, Bifidobacteria, Lactobacillus casei, Lactobacillus rhamnosus, and Propionibacteria," Journal of Dairy Science, 86: 2288-2296 (2003).
Sohier et al., "Evolution of microbiological analytical methods for dairy industry needs," Frontiers in Microbiology, 5: 16-1 (2014).
Zotta et al., "A comparison of fluorescent stains for the assessment of viability and metabolic activity of lactic acid bacteria," World Journal of Microbiology and Biotechnology, 28: 919-927 (2011).
International Search Report issued in corresponding International Patent Application No. PCT/FR2014/053359 dated Mar. 26, 2015.

* cited by examiner

*Primary Examiner* — Bin Shen
(74) *Attorney, Agent, or Firm* — Morgan, Lewis & Bockius LLP

(57) ABSTRACT

The invention relates to a method for distinguishing between and enumerating strains of lactic acid bacteria or Bifidobacteria present in a food product. This method implements various agar culture media and/or selective culture conditions, combined with various chromogenic substrates.

12 Claims, No Drawings

METHOD FOR THE DIFFERENTIAL ENUMERATION OF LACTIC ACID BACTERIA IN A MIXTURE IN A FOOD PRODUCT

The present invention relates to the differentiation and counting of bacterial strains of interest present in a mixture in a food product, especially a dairy product.

In the manufacture of fermented products, and especially dairy products, mixtures of bacteria which may comprise bacteria of different genera, and/or bacteria of the same genus and of different species or subspecies, and/or different strains of bacteria of the same species or subspecies, are generally used as ferments. In particular, probiotic products usually comprise, aside from one or more probiotic strains, one or more "technological" strains which do not necessarily have probiotic properties but enable, for example, the growth of the probiotic strains to be improved, and/or make it possible to confer the desired properties (flavor, texture, etc.) on the finished product.

So as to guarantee the quality of the fermented products during their manufacture, at the end of their manufacture and during their storage, it is necessary to be able to specifically differentiate and count the probiotic and technological bacterial strains present in these products, which may be problematic especially in cases in which at least two of the strains used in the product belong to neighboring species of the same genus, or to the same species or even to the same subspecies.

It is therefore desirable to have reliable and rapid analytical techniques which enable the differential counting of these strains.

The inventors have now developed a method based on the use of selective culture media and/or selective culture conditions, combined with the use of different chromogenic substrates.

Consequently, the subject of the present invention is a method for distinguishing from one another, and counting, strains of lactic acid bacteria or Bifidobacteria of a known mixture, which are present in different population amounts in a food product, preferably a dairy product, fermented using said strains, characterized in that it comprises:

a) inoculating aliquots of the optionally diluted food product in a series of culture dishes containing a chemically defined agar M1 medium and at least two chromogenic substrates producing different colorations, each of said substrates being taken up by at least one of said bacterial strains, and not being taken up by at least one other of said strains;

b) optionally, inoculating aliquots of the optionally diluted food product in a series of culture dishes containing a chemically defined agar M2 medium enabling the growth of the lactic acid bacterial strains present in the product to be tested, which strains cannot grow on the M1 medium, and at least one chromogenic substrate taken up by at least one of said bacterial strains;

c) incubating said dishes for the time necessary to form bacterial colonies, and counting the colonies for each of the colorations observed in each culture dish.

Within the meaning of the invention, the expression "lactic acid bacteria or Bifidobacteria" preferably refers to all anaerobic, partially oxygen-tolerant Gram positive bacteria which generally do not produce spores, which bacteria are in rod or coccus form and are capable of fermenting sugars to lactic acid. More preferably, the lactic acid bacteria within the meaning of the invention belong to at least one of the families Aerococcaceae, Carnobacteriaceae, Enterococcaceae, Lactobacillaceae, Leuconostocaceae, Streptococcaceae or Bifidobacteriaceae, and even more preferably to one of the genera *Aerococcus, Carnobacterium, Enterococcus, Lactobacillus, Lactococcus, Leuconostoc, Oenococcus, Pediococcus, Streptococcus, Tetragenococcus, Vagococcus, Weissella* or *Bifidobacterium*. Most particularly preferably, the lactic acid bacteria or Bifidobacteria within the meaning of the invention belong to at least one of the species *Lactobacillus brevis, Lactobacillus buchneri, Lactobacillus casei, Lactobacillus curvatus, Lactobacillus delbruckei*, in particular *L. delbruckei* supsb. *bulgaricus* or *lactis, Lactobacillus diolivorans, Lactobacillus fermentum, Lactobacillus fructivorans, Lactobacillus helveticus, Lactobacillus hilgardii, Lactobacillus jensenii, Lactobacillus kunkeei, Lactobacillus mall, Lactobacillus nagelii, Lactobacillus paracasei*, in particular *L. paracasei* subsp. *paracasei, Lactobacillus plantarum, Lactobacillus vini, Lactobacillus rhamnosus, Streptococcus thermophilus, Streptococcus lactis, Streptococcus raffinolactis, Streptococcus cremoris, Bifidobacterium adolescentis, Bifidobacterium animalis, Bifidobacterium bifidum, Bifidobacterium breve, Bifidobacterium infantis, Bifidobacterium lactis*, or *Bifidobacterium longum*; the Bifidobacteria within the meaning of the invention gather the bacteria belonging to the family Bifidobacteriaceae, especially to the genus *Bifidobacterium*.

"Known mixture" is intended to mean a mixture of bacterial strains, the qualitative composition of which is known, that is to say the nature and the characteristics of the different strains which constitute it. It relies more specifically to the mixture of strains used for the manufacture of the fermented product on which the analysis is based. Before carrying out the method in accordance with the invention, these strains will have been subjected to a phenotypic analysis with the aim of highlighting their physiological and metabolic characteristics, so as to establish a phenotypic profile specific to each strain. This analysis may especially relate to the use of different types of sources of carbon, nitrogen, phosphate and sulfur, to the use of given nutritional additives, and/or to the resistance to different stressing agents (salts, pH, antimicrobial agents, etc.).

The term "chemically defined medium" is used here in its usual sense, to denote a culture medium, all the components of which are entirely known and defined. The chemically defined agar medium according to the invention is preferably an agar bacterial culture medium, more preferably an agar culture medium for lactic acid bacteria or Bifidobacteria.

As it is intended here, the expression "chromogenic substrate" preferably denotes a substrate, the uptake of which by a bacterium produces a substance that absorbs light at one or more wavelengths, especially a colored substance. As those skilled in the art will well appreciate, the wavelength(s) absorbed by the substance produced are preferably different to that (those) optionally absorbed by the chromogenic substrate, which may especially be colorless. Chromogenic substrates which may be used to carry out the present invention are known per se; they may be, especially, 6-chloro-3-indoxyl-β-D-galactopyranoside (salmon Gal), 5-bromo-4-chloro-3-indolyl-β-D-glucopyranoside (X-Glu), 5-bromo-4-chloro-3-indolyl-β-D-galactopyranoside (X-Gal).

The agar medium of a portion of the culture dishes may also comprise at least one additive selectively promoting the growth of at least one of said bacterial strains, and/or the agar medium of a portion of the culture dishes may also comprise at least one additive selectively inhibiting the growth of at least one of said bacterial strains.

Also, a portion of the culture dishes may be incubated under selective conditions favorable to the growth of at least one of said bacterial strains, and another portion of said culture dishes may be incubated under different selective conditions favorable to the growth of at least one other of said bacterial strains.

The method in accordance with the invention is particularly suited to the analysis of products in which at least two of the present bacterial strains belong to the same species and subspecies.

Preferably, at least one of the bacterial strains present in the product to be tested belongs to the genus *Lactobacillus* and/or at least one of the bacterial strains present in the product to be tested belongs to the genus *Streptococcus*.

According to a particular embodiment of the present invention, the product to be tested contains at least one strain of *Lactobacillus paracasei* subsp. *paracasei*, at least one strain of *Lactobacillus delbrueckii* subsp. *bulgaricus*, and at least one strain of *Streptococcus thermophilus*. Advantageously, it also contains at least one strain of *Lactobacillus rhamnosus*.

Within the context of this embodiment, to count the bacteria of the species *Lactobacillus paracasei* subsp. *paracasei*, *Lactobacillus rhamnosus*, and *Streptococcus thermophilus*, a M1 medium with the following composition is used: agar: 15 g/l; tryptone: 2.5 g/l; pepsin-digested meat peptone: 2.5 g/l; papain-digested soya peptone: 5 g/l; sodium glycerophosphate: 19 g/l; lactose: 5 g/l; yeast extract: 2.5 g/l; meat extract: 5 g/l; magnesium sulfate: 0.25 g/l; ascorbic acid: 0.5 g/l; 6-chloro-3-indoxyl-β-D-galactopyranoside (salmon Gal): 0.2 g/l; 5-bromo-4-chloro-3-indolyl-β-D-glucopyranoside (X-Glu): 0.1 g/l.

To count the bacteria of the species *Lactobacillus delbrueckii* subsp. *bulgaricus*, a M2 medium with the following composition is used: polypeptone: 10 g/l; yeast extract: 5 g/l; meat extract: 10 g/l; dipotassium phosphate: 2 g/l; sodium acetate: 5 g/l; ammonium citrate: 2 g/l; magnesium sulfate: 0.2 g/l; manganese sulfate: 0.05 g/l; agar: 15 g/l; 5-bromo-4-chloro-3-indolyl-β-D-galactopyranoside (X-Gal): 0.15 g/l.

Advantageously, to count the bacteria of the species *Lactobacillus paracasei* subsp. *paracasei*, *Lactobacillus rhamnosus*, and *Streptococcus thermophilus*:
- a first portion of the dishes containing the M1 medium does not comprise any additive, a second portion of said dishes comprises vancomycin as an additive, and a third portion of said dishes comprises rhamnose as an additive; and/or
- the inoculated dishes are incubated for approximately 48 hours under a controlled atmosphere containing from 6 to 16% $O_2$ and from 2 to 10% $CO_2$, a portion of said dishes being incubated at approximately 37° C., and another portion at approximately 44° C.

Preferably, to count the bacteria of the species *Lactobacillus delbrueckii* subsp. *Bulgaricus*, the inoculated dishes of M2 medium are incubated for approximately 48 hours at approximately 47° C. under a controlled atmosphere containing less than 1% $O_2$ and at least 13% $CO_2$.

The present invention will be better understood by means of the following additional description which makes reference to nonlimiting examples illustrating carrying out a method in accordance with the invention to differentiate different strains of lactic acid bacteria and to count the bacteria of each of these strains in fermented dairy products.

EXAMPLE DIFFERENTIAL COUNTING OF LACTIC ACID BACTERIA IN FERMENTED DAIRY PRODUCTS

Materials and Methods:
Composition of the Products Tested
Product 1:
Product 1 is a fermented product containing 5 bacterial strains belonging to three species, namely:
  1 probiotic strain of *L. casei* subsp. *paracasei* (hereinafter referred to as *Lactobacillus paracasei* strain 1);
  3 technological strains of *S. thermophilus*;
  1 technological strain of *L. delbrueckii* subsp. *Bulgaricus*.

The theoretical bacterial loads expected at the start of the self life (D4) and at the end of the, self life (D35) of the product are indicated in table I below.

TABLE I

| | Theoretical bacterial load (in bacteria/ml) | |
|---|---|---|
| | D4 | D35 |
| *Lactobacillus paracasei* strain 1 | $2 \times 10^8$ | $2 \times 10^8$ |
| 3 *Streptococcus thermophilus* | $>10^8$ | $>10^8$ |
| *Lactobacillus bulgaricus* | $1 \times 10^7$ | $10^1$ to $10^4$ |

Product 2:
Product 2 is a fermented product containing 7 bacterial strains belonging to three species, namely:
  2 probiotic strains of *L. casei* subsp. *paracasei* (*Lactobacillus paracasei* strain 1 and *Lactobacillus paracasei* strain 2);
  1 probiotic strain of *L. rhamnosus*;
  3 technological strains of *S. thermophilus*;
  1 technological strain of *L. delbrueckii* subsp. *Bulgaricus*.

The theoretical bacterial loads expected at the beginning of the shelf life (D4) and at the end of the shelf life (D35) of the product are indicated in table II below.

TABLE II

| | Theoretical bacterial load (in bacteria/ml) | |
|---|---|---|
| | D4 | D35 |
| *Lactobacillus paracasei* strain 1 and strain 2 | 2 to $3 \times 10^8$ | 2 to $3 \times 10^8$ |
| *Lactobacillus rhamnosus* | $1 \times 10^8$ | $1 \times 10^8$ |
| 3 *Streptococcus thermophilus* | $1 \times 10^8$ | $1 \times 10^8$ |
| *Lactobacillus bulgaricus* | $1 \times 10^7$ | $10^1$ to $10^4$ |

Enzymatic Activities of the Strains:
The different strains were tested for their β-glucosidase and β-galactosidase activities.
The results are indicated in table III below.

TABLE III

| Strain | β-Glucosidase | β-Galactosidase |
|---|---|---|
| *Lactobacillus rhamnosus* | + | + |
| *Lactobacillus paracasei* 1 | + | − |
| *Lactobacillus paracasei* 2 | − | − |
| *Streptococcus thermophilus* 1 | − | + |
| *Streptococcus thermophilus* 2 | − | + |
| *Streptococcus thermophilus* 3 | − | + |
| *Lactobacillus bulgaricus* | − | + |

Bacteria Counting in Products 1 and 2:

Culture Conditions and Media:

The culture conditions and media currently used for counting bacterial strains present in products 1 and 2 are summarized in tables IV and V, respectively, below. These reference culture conditions and media were used as controls.

TABLE IV

| Strain studied | Medium | Temperature | Duration | Atmosphere |
| --- | --- | --- | --- | --- |
| Lactobacillus paracasei 1 | MRS + vancomycin (1 µg/ml) | 37° C. | 48 hours | $CO_2$ |
| Streptococcus sp. | M17 | 44° C. | 48 hours | Aerobic |
| Lactobacillus bulgaricus | Acid MRS | 50° C. | 48 hours | Anaerobic |

TABLE V

| Strain studied | Medium | Temperature | Duration | Atmosphere |
| --- | --- | --- | --- | --- |
| Lactobacillus rhamnosus | MRS + vancomycin (1 µg/ml) | 44° C. | 48 hours | $CO_2$ |
| Lactobacillus rhamnosus + Lactobacillus paracasei 1 + Lactobacillus paracasei 2 | MRS + vancomycin (1 µg/ml) | 37° C. | 48 hours | $CO_2$ |
| Streptococcus sp. | M17 | 44° C. | 48 hours | Aerobic |
| Lactobacillus bulgaricus | Acid MRS | 50° C. | 48 hours | Anaerobic |

The MRS, acid MRS and M17 media are conventional commercially available media (AES CHEMUNEX).

For the cultures under a controlled atmosphere, GAS-PAK® gas generating systems were used to obtain the following conditions:

anaerobic conditions: % $O_2$<1%; % $CO_2$≥13%

$CO_2$: % $CO_2$>2.5% microaerobic conditions: 6%<% $O_2$<16%; 2%<% $CO_2$<10% aerobic conditions: ambient air

Two chromogenic media, hereinafter referred to as M1 and M2, were prepared: the composition of these media is indicated in tables VI and VII below, respectively:

TABLE VI

M1 Medium

| Constituent | Concentration (in g/l) |
| --- | --- |
| Agar | 15 |
| Tryptone | 2.5 |
| Pepsin-digested meat peptone | 2.5 |
| Papain-digested soya peptone | 5 |
| Sodium glycerophosphate | 19 |
| Lactose | 5 |
| Yeast extract | 2.5 |
| Meat extract | 5 |
| Magnesium sulfate | 0.25 |
| Ascorbic acid | 0.5 |
| 6-Chloro-3-indoxyl-β-D-galactopyranoside (salmon Gal) | 0.2 |
| 5-Bromo-4-chloro-3-indolyl-β-D-glucopyranoside (X-Glu) | 0.1 |

TABLE VII

M2 Medium

| Constituent | Concentration (in g/l) |
| --- | --- |
| Polypeptone | 10 |
| Yeast extract | 5 |
| Meat extract | 10 |
| Dipotassium phosphate | 2 |
| Sodium acetate | 5 |
| Ammonium citrate | 2 |
| Magnesium sulfate | 0.2 |
| Manganese sulfate | 0.05 |
| Agar | 15 |
| 5-Bromo-4-chloro-3-indolyl-β-D-galactopyranoside (X-Gal) | 0.15 |

The tests were carried out with 3 different batches of each of the M1 and M2 media.

The culture conditions used for products 1 and 2 are respectively indicated in tables VIII and IX below:

TABLE VIII

| Strain studied | Medium | Temperature | Duration | Atmosphere |
| --- | --- | --- | --- | --- |
| Lactobacillus paracasei 1 + Streptococcus sp. | M1 | 37° C. | 48 hours | Microaerobic |
| Lactobacillus bulgaricus | M2 | 47° C. | 48 hours | Anaerobic |

TABLE IX

| Strain studied | Medium | Temperature | Duration | Atmosphere |
| --- | --- | --- | --- | --- |
| Lactobacillus paracasei 1 | M1 + rhamnose (10 g/l) | 37° C. | 48 hours | Microaerobic |
| Lactobacillus paracasei 2 | M1 + vancomycin (1 µg/ml) | 37° C. | 48 hours | Microaerobic |
| Lactobacillus rhamnosus + Streptococcus sp. | M1 | 44° C. | 48 hours | Microaerobic |
| Lactobacillus bulgaricus | M2 | 47° C. | 48 hours | Anaerobic |

Operating Protocol:

Samples were taken at two self life phases of the products: start of life and end of life.

For product 1, start of self life samples were taken at 4, 5 and 6 days after the manufacture of the fermented product, and end of self life samples were taken at 31, 32 and 33 days after the manufacture; for product 2, start of self life samples were taken at 7, 8 and 9 days after the manufacture, and end of self life samples were taken at 28, 29 and 30 days after the manufacture.

For each test specimen, a range of dilutions to ¹/₁₀ was carried out in tryptone salt tubes. Three dilutions, chosen as a function of the theoretical populations (cf. Tables I and II), were inoculated on each of the media used. For each dilution, 1 ml of diluted product was inoculated in 1 Petri dish, and 15 ml of the medium used were poured into the dish.

The dishes were incubated under the conditions, and for the durations, indicated in tables IV, V, VIII and IX.

Results:

Identification of the Strains:

On M1 medium:
- at 44° C., the *Lactobacillus rhamnosus* strain produces blue-colored colonies, and the *Streptococcus thermophilus* strains produce magenta-colored colonies; the *Lactobacillus paracasei* strains 1 and 2 and the *Lactobacillus bulgaricus* strain do not grow;
- at 37° C. with addition of rhamnose, the *Lactobacillus rhamnosus* strain and the *Lactobacillus paracasei* strain 2 produce colorless colonies; the *Lactobacillus paracasei* strain 1 produces turquoise-colored colonies and the *Streptococcus thermophilus* strains produce magenta-colored colonies. The *Lactobacillus bulgaricus* strain does not grow;
- at 37° C. with addition of vancomycin, the *Lactobacillus rhamnosus* strain produces blue colonies; the *Lactobacillus paracasei* strain 1 produces turquoise-colored colonies and the *Lactobacillus paracasei* strain 2 produces colorless colonies; the *Streptococcus thermophilus* strains and the *Lactobacillus bulgaricus* strain do not grow.

On M2 medium:
- the *Lactobacillus rhamnosus* strain produces colorless colonies, and the *Lactobacillus bulgaricus* strain produces blue colonies. The *Streptococcus thermophilus* strains and the *Lactobacillus paracasei* strains 1 and 2 do not grow.

These results are summarized in table X below:

TABLE X

| | M1 Medium | | | |
| --- | --- | --- | --- | --- |
| Name of strain | Incubation at 44° C. | Addition of rhamnose and incubation at 37° C. | Addition of vancomycin and incubation at 37° C. | M2 Medium |
| *Lactobacillus rhamnosus* | Blue | Colorless | Blue | Colorless |
| *Lactobacillus paracasei* 1 | Absence of growth | Turquoise | Turquoise | Absence of growth |
| *Lactobacillus paracasei* 2 | Absence of growth | Colorless | Colorless | Absence of growth |
| *Streptococcus thermophilus* (strains 1, 2, and 3) | Magenta | Magenta | Absence of growth | Absence of growth |
| *Lactobacillus bulgaricus* | Absence of growth | Absence of growth | Absence of growth | Blue |
| Strain(s) identified | *Lactobacillus rhamnosus* and *Streptococcus thermophilus* | *Lactobacillus paracasei* 1 | *Lactobacillus paracasei* 2 | *Lactobacillus bulgaricus* |

Product 1:
  M1 Medium therefore makes it possible to count *Lactobacillus paracasei* and *Streptococcus thermophilus*, and M2 medium makes it possible to count *Lactobacillus bulgaricus*.

Product 2:
  M1 Medium therefore makes it possible to count:
  at 44° C.: *Lactobacillus rhamnosus* and *Streptococcus thermophilus*
  with addition of rhamnose at 37° C.: *Lactobacillus paracasei* strain 1;
  with addition of vancomycin at 37° C.: *Lactobacillus paracasei* strain 2.
  M2 Medium makes it possible to count *Lactobacillus bulgaricus*.

Bacteria Counting Bacteria:

Product 1:

Early in Self Life:
  The results are illustrated in table XI.

TABLE XI

| Species | | Reference medium (control) | Batch 1 | Batch 2 | Batch 3 |
| --- | --- | --- | --- | --- | --- |
| *L. paracasei* 1 | Bacterial load | $5.4 \times 10^8$ | $6.1 \times 10^8$ | $5.7 \times 10^8$ | $6.2 \times 10^8$ |
| | Difference vs. control (log) | | +0.06 | +0.03 | +0.07 |
| *S. thermophilus* | Bacterial load | $6.4 \times 10^8$ | $5.3 \times 10^8$ | $6.8 \times 10^8$ | $5.5 \times 10^8$ |
| | Difference vs. control (log) | | −0.08 | +0.03 | −0.07 |

TABLE XI-continued

| Species | | Reference medium (control) | Batch 1 | Batch 2 | Batch 3 |
|---|---|---|---|---|---|
| L. bulgaricus | Bacterial load | $1.6 \times 10^{6}$* | $3 \times 10^{6}$ | $3 \times 10^{6}$ | $2.8 \times 10^{6}$ |
| | Difference vs. control (log) | | +0.27 | +0.26 | 0.23 |

The variability of the counting method is as follows:
On M1 medium: between $5.7 \times 10^{8}$ CFU/ml and $6.2 \times 10^{8}$ CFU/ml for *L. paracasei* 1, between $5.3 \times 10^{8}$ CFU/ml and $6.8 \times 10^{8}$ CFU/ml for *S. thermophilus*,
On M2 medium: between $2.8 \times 10^{6}$ CFU/ml and $3 \times 10^{6}$ CFU/ml for *L. bulgaricus*.

Difficulties in counting *L. bulgaricus* on the reference medium, acid MRS, are to be noted:
- day 5: difference of one log versus medium M2 and the count from D4,
- day 6: absence of growth.

End of Self Life:
The results are illustrated in table XII.

TABLE XII

| Species | | Reference medium (control) | Batch 1 | Batch 2 | Batch 3 |
|---|---|---|---|---|---|
| L. paracasei 1 | Bacterial load | $4.5 \times 10^{8}$ | $4.1 \times 10^{8}$ | $4 \times 10^{8}$ | $4.5 \times 10^{8}$ |
| | Difference vs. control (log) | | −0.04 | −0.05 | −0.01 |
| S. thermophilus | Bacterial load | $1.8 \times 10^{8}$ | $1.9 \times 10^{8}$ | $1.9 \times 10^{8}$ | $2.2 \times 10^{8}$ |
| | Difference vs. control (log) | | +0.02 | +0.02 | +0.08 |
| L. bulgaricus | Bacterial load | Absence | Absence | Absence | Absence |
| | Difference vs. control (log) | | N.A. | N.A. | N.A. |

M1 Medium makes it possible to effectively discriminate between *Lactobacillus paracasei* and *Streptococcus thermophilus* present in the product. The counts for *L. paracasei* vary between $4 \times 10^{8}$ CFU/ml and $4.5 \times 10^{8}$ CFU/ml over the three batches and over three days of analysis. The load of *S. thermophilus* varies between $1.9 \times 10^{8}$ CFU/ml and $2.2 \times 10^{8}$ CFU/ml.

These tests also demonstrate the absence of *L. bulgaricus* in the product at this lifetime stage, whether on the reference medium or on M2 medium.

Product 2:
Early in Self Life:
The results are illustrated in table XIII.

TABLE XIII

| Species | | Reference medium (control) | Batch 1 | Batch 2 | Batch 3 |
|---|---|---|---|---|---|
| L. paracasei 1 and 2 | L. paracasei 1 bacterial load | $2 \times 10^{8}$ | $1.6 \times 10^{8}$ | $1.8 \times 10^{8}$ | $1.7 \times 10^{8}$ |
| | L. paracasei 2 bacterial load | | $2.3 \times 10^{7}$ | $3 \times 10^{7}$ | $2.8 \times 10^{7}$ |
| | Difference vs. control (log) | | −0.02 | +0.03 | 0.00 |
| S. thermophilus | Bacterial load | $8.9 \times 10^{8}$ | $8.7 \times 10^{8}$ | $9.1 \times 10^{8}$ | $9.8 \times 10^{8}$ |
| | Difference vs. control (log) | | −0.01 | +0.01 | +0.04 |
| L. rhamnosus | Bacterial load | $2.3 \times 10^{8}$ | $2.3 \times 10^{8}$ | $2.3 \times 10^{8}$ | $2.3 \times 10^{8}$ |
| | Difference vs. control (log) | | 0.00 | 0.00 | 0.00 |
| L. bulgaricus | Bacterial load | $2.5 \times 10^{5}$ | $4.6 \times 10^{5}$ | $2.6 \times 10^{5}$ | $3.1 \times 10^{5}$ |
| | Difference vs. control (log) | | +0.27 | +0.03 | 0.10 |

The variability of the counting method is as follows:
On M1 medium: between $1.6 \times 10^8$ CFU/ml and $1.8 \times 10^8$ CFU/ml for *L. paracasei* 1, between $2.3 \times 10^7$ CFU/ml and $3 \times 10^7$ CFU/ml for *L. paracasei* 2, between $8.7 \times 10^8$ CFU/ml and $9.8 \times 10^8$ CFU/ml for *S. thermophilus*, $2.3 \times 10^8$ CFU/ml for the three batches for *L. rhamnosus*
On M2 medium: between $2.6 \times 10^5$ CFU/ml and $5 \times 10^5$ CFU/ml for *L. bulgaricus*.

End of Self Life:
The results are illustrated in table XIV.

TABLE XIV

| Species | | Reference medium (control) | Batch 1 | Batch 2 | Batch 3 |
|---|---|---|---|---|---|
| *L. paracasei* 1 and 2 | *L. paracasei* 1 bacterial load | $2.1 \times 10^8$ | $1.6 \times 10^8$ | $1.5 \times 10^8$ | $1.6 \times 10^8$ |
| | *L. paracasei* 2 bacterial load | | $1.4 \times 10^7$ | $2.2 \times 10^7$ | $2.2 \times 10^7$ |
| | Difference vs. control (log) | | −0.07 | −0.08 | −0.05 |
| *S. thermophilus* | Bacterial load | $7.3 \times 10^8$ | $6.8 \times 10^8$ | $6.6 \times 10^8$ | $7.5 \times 10^8$ |
| | Difference vs. control (log) | | −0.03 | −0.04 | +0.01 |
| *L. rhamnosus* | Bacterial load | $1.8 \times 10^8$ | $2.0 \times 10^8$ | $2.0 \times 10^8$ | $2.0 \times 10^8$ |
| | Difference vs. control (log) | | +0.03 | +0.04 | +0.04 |
| *L. bulgaricus* | Bacterial load | Absence | Absence | Absence | Absence |
| | Difference vs. control (log) | | N.A. | N.A. | N.A. |

The counts over the three batches of M1 medium vary between $1.5 \times 10^8$ CFU/ml and $1.6 \times 10^8$ CFU/ml for *L. paracasei* 1, between $1.4 \times 10^7$ CFU/ml and $2.2 \times 10^7$ CFU/ml for *L. paracasei* 2, between $6.6 \times 10^8$ CFU/ml and $7.5 \times 10^8$ CFU/ml for *S. thermophilus*, $2.0 \times 10^8$ CFU/ml for the three batches for *L. rhamnosus*.

The tests also demonstrate the absence of *L. bulgaricus* in the product at this lifetime stage, whether on the reference medium or on M2 medium.

Use of the method described above makes it possible to discriminate between the three bacterial species present in product 1 and the four present in product 2.

The invention claimed is:

1. A method for distinguishing from one another, and counting, strains of lactic acid bacteria or Bifidobacteria in a known mixture, which are present in different population amounts in a dairy product,
   wherein the diary product to be tested contains at least one strain of *Lactobacillus paracasei* subsp. *paracasei*, at least one strain of *Lactobacillus delbrueckii* subsp. *bulgaricus*, and at least one strain of *Streptococcus thermophilus*,
   wherein the method comprises:
   (a) inoculating aliquots of said food product in a series of culture dishes each containing a chemically defined agar M1 medium with the following composition: agar 15 g/l, tryptone 2.5 g/l, pepsin-digested meat peptone 2.5 g/l, papain-digested soya peptone 5 g/l, sodium glycerophosphate 19 g/l, lactose 5 g/l, yeast extract 2.5 g/l, meat extract 5 g/l, magnesium sulfate 0.25 g/l, ascorbic acid 0.5 g/l; and at least two chromogenic substrates: 6-chloro-3-indoxyl-β-D-galactopyranoside (salmon Gal) 0.2 g/l and 5-bromo-4-chloro-3-indolyl-β-D-glucopyranoside (X-Glu) 0.1 g/l producing different colorations, each of said substrates being taken up by at least one of said bacterial strains, and not being taken up by at least one other of said strains; and
   (b) optionally, inoculating aliquots of said food product in a series of culture dishes containing a chemically defined agar M2 medium enabling the growth of the lactic acid bacterial strains present in the product to be tested, which strains cannot grow on the M1 medium, and at least one chromogenic substrate taken up by at least one of said bacterial strains; and
   (c) incubating said dishes for the time necessary to form bacterial colonies, and counting the colonies for each of the colorations observed in each culture dish.

2. The method according to claim 1, wherein the agar medium of a portion of the culture dishes also comprises at least one additive selectively promoting the growth of at least one of said bacterial strains, and/or the agar medium of a portion of the culture dishes also comprises at least one additive selectively inhibiting the growth of at least one of said bacterial strains.

3. The method according to claim 2, wherein a portion of said culture dishes is incubated under selective conditions favorable to the growth of at least one of said bacterial strains, and another portion of the culture dishes is incubated under different selective conditions favorable to the growth of at least one other of said bacterial strains.

4. The method according to claim 2, wherein at least two of the bacterial strains present in the product to be tested belong to the same species and subspecies.

5. The method according to claim 1, wherein a portion of said culture dishes is incubated under selective conditions favorable to the growth of at least one of said bacterial strains, and another portion of the culture dishes is incubated under different selective conditions favorable to the growth of at least one other of said bacterial strains.

6. The method according to claim 5, wherein at least two of the bacterial strains present in the product to be tested belong to the same species and subspecies.

7. The method according to claim 1, wherein at least two of the bacterial strains present in the product to be tested belong to the same species and subspecies.

8. The method according to claim 1, wherein the product to be tested also contains at least one strain of *Lactobacillus rhamnosus*.

9. The method according to claim 8, wherein to count the bacteria of the species *Lactobacillus delbrueckii bulgaricus*, a M2 medium with the following composition is used: polypeptone: 10 g/l; yeast extract: 5 g/l; meat extract: 10 g/l; dipotassium phosphate: 2 g/l; sodium acetate: 5 g/l; ammonium citrate: 2 g/l; magnesium sulfate: 0.2 g/l; manganese sulfate: 0.05 g/l; agar: 15 g/l; 5-bromo-4-chloro-3-indolyl-β-D-galactopyranoside (X-Gal): 0.15 g/l.

10. The method according to claim 8, wherein to count the bacteria of the species *Lactobacillus paracasei* subsp. *paracasei*, *Lactobacillus rhamnosus*, and *Streptococcus thermophilus*, a first portion of the dishes containing the M1 medium does not comprise any additive, a second portion of said dishes comprises vancomycin as an additive, and a third portion of said dishes comprises rhamnose as an additive.

11. The method according to claim 8, wherein to count the bacteria of the species *Lactobacillus paracasei* subsp. *paracasei*, *Lactobacillus rhamnosus*, and *Streptococcus thermophilus*, the inoculated dishes are incubated for approximately 48 hours under a controlled atmosphere containing from 6 to 16% $O_2$ and from 2 to 10% $CO_2$, a portion of said dishes being incubated at approximately 37° C., and another portion at approximately 44° C.

12. The method according to claim 8, wherein to count the bacteria of the species *Lactobacillus delbrueckii bulgaricus*, the inoculated dishes are incubated for approximately 48 hours at approximately 47° C. under a controlled atmosphere containing less than 1% $O_2$ and at least 13% $CO_2$.

* * * * *